US009505002B2

(12) United States Patent
Momboisse et al.

(10) Patent No.: US 9,505,002 B2
(45) Date of Patent: Nov. 29, 2016

(54) INCUBATOR

(71) Applicant: INHECO INDUSTRIAL HEATING AND COOLING GMBH, Martinsried (DE)

(72) Inventors: Michel Momboisse, Munich (DE); Christian George, Wolfratshausen (DE); Volker Lob, Munich (DE)

(73) Assignee: INHECO INDUSTRIAL HEATING AND COOLING GMBH, Martinsried (DE)

( * ) Notice: Subject to any disclaimer, the term of this patent is extended or adjusted under 35 U.S.C. 154(b) by 0 days.

(21) Appl. No.: 14/793,320

(22) Filed: Jul. 7, 2015

(65) Prior Publication Data

US 2015/0306600 A1 Oct. 29, 2015

Related U.S. Application Data

(63) Continuation of application No. PCT/EP2013/003735, filed on Dec. 11, 2013.

(30) Foreign Application Priority Data

Jan. 7, 2013 (DE) .................. 10 2013 000 044

(51) Int. Cl.
*C12M 1/00* (2006.01)
*B01L 7/00* (2006.01)
(Continued)

(52) U.S. Cl.
CPC .. *B01L 7/00* (2013.01); *B01L 9/00* (2013.01); *C12M 23/04* (2013.01); *C12M 23/48* (2013.01);
(Continued)

(58) Field of Classification Search
CPC ......... G01N 2035/00356; B01L 7/00; C12M 23/50
See application file for complete search history.

(56) References Cited

U.S. PATENT DOCUMENTS

| | | | | |
|---|---|---|---|---|
| 5,265,951 A | * | 11/1993 | Kumar | ................ G06F 15/0216 312/223.2 |
| 2004/0152188 A1 | | 8/2004 | Yamamoto et al. | |
| 2005/0051723 A1 | | 3/2005 | Neagle et al. | |

FOREIGN PATENT DOCUMENTS

| | | |
|---|---|---|
| DE | 102005036763 A1 | 2/2007 |
| FR | 2849862 A1 | 7/2004 |

(Continued)

OTHER PUBLICATIONS

International Search Report with Written Opinion, mailed Mar. 26, 2014, for corresponding international application PCT/EP2013/003735.

*Primary Examiner* — Jyoti Nagpaul
(74) *Attorney, Agent, or Firm* — Myers Wolin, LLC

(57) ABSTRACT

An incubator is provided for exposing samples accommodated in sample containers to a specifically specifiable temperature, comprising a sample chamber, the temperature of which can be controlled and which has at least one closable access opening, and at least one insertion and removal mechanism, which bears a sample container carrier and by means of which the sample container carrier, which in turn bears a sample container, can be moved into the sample chamber and out of the sample chamber through an access opening of the incubator. The incubator according to the invention is furthermore characterized in that the at least one insertion and removal mechanism is installed completely outside of the sample chamber and bears the sample container carrier inserted into the sample chamber even while the access opening is closed.

14 Claims, 5 Drawing Sheets

(51) Int. Cl.
*B01L 9/00* (2006.01)
*C12M 1/12* (2006.01)
*C12M 3/00* (2006.01)

(52) U.S. Cl.
CPC ............. *C12M 23/50* (2013.01); *C12M 41/14* (2013.01); *B01L 2300/04* (2013.01); *B01L 2300/0609* (2013.01); *B01L 2300/0848* (2013.01); *B01L 2300/18* (2013.01)

(56) References Cited

FOREIGN PATENT DOCUMENTS

| | | | |
|---|---|---|---|
| JP | 2004267117 A | | 9/2004 |
| JP | 2006149232 A | | 9/2004 |
| WO | WO2010/130762 | * | 11/2010 |
| WO | 2012141055 A1 | | 10/2012 |

* cited by examiner

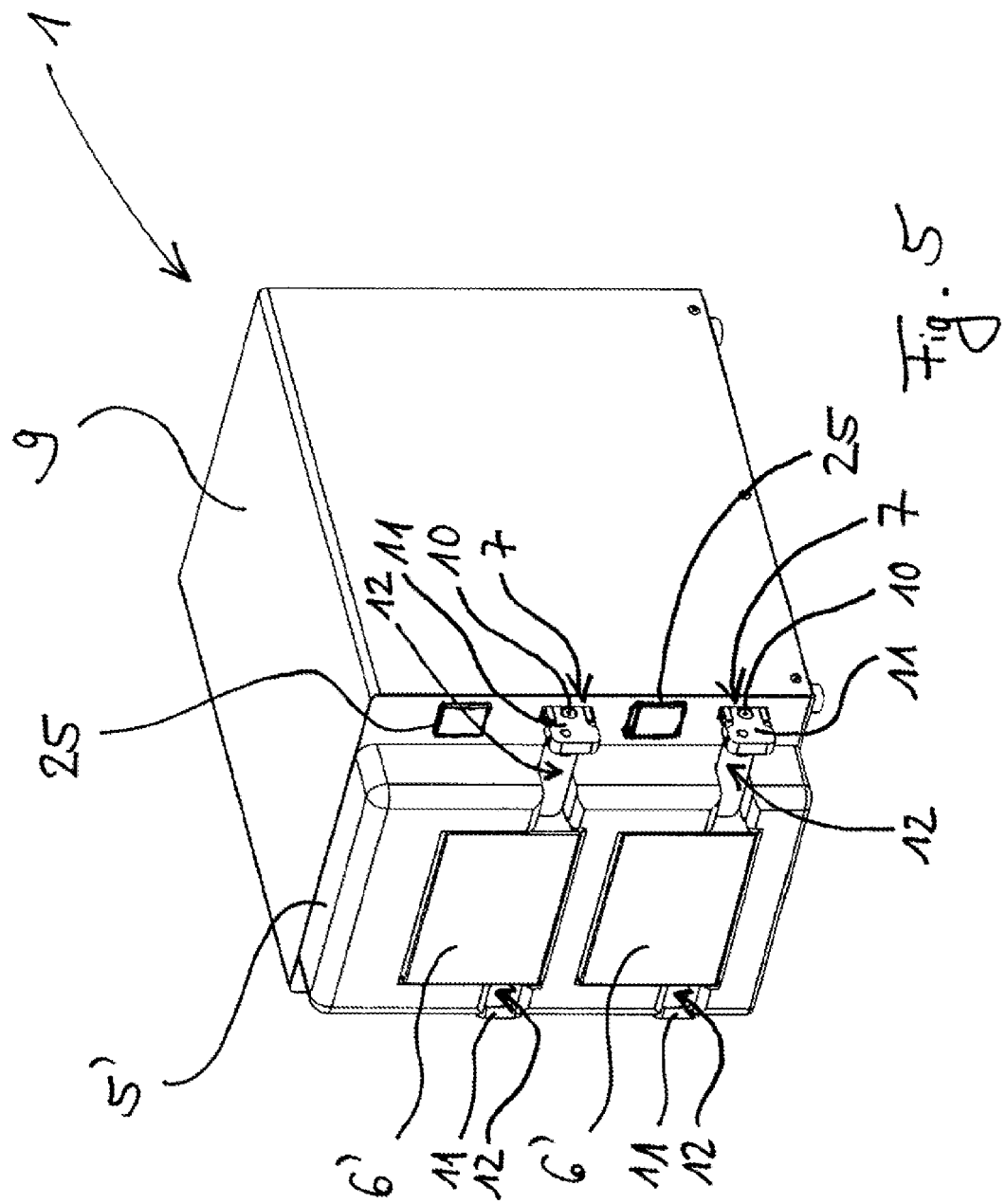

INCUBATOR

CROSS REFERENCE TO RELATED APPLICATIONS

This application is a continuation under 35 U.S.C. §120 of International Application PCT/EP2013/003735, filed Dec. 11, 2013, which claims priority to German Application 10 2013 000 044.0, filed Jan. 7, 2013, the contents of each of which are incorporated by reference herein.

FIELD OF THE INVENTION

The present invention relates to an incubator for exposing samples accommodated in sample containers to a specifically specifiable temperature, comprising a temperature-regulatable sample chamber, which has at least one closable access opening and at least one insertion and removal mechanism, which bears a sample container carrier and by means of which the sample container carrier, which in turn bears a sample container, can be moved into the sample chamber and out of the latter through an access opening of the incubator.

BACKGROUND

Incubators of the aforementioned type are sufficiently known from the state of the art, for example from DE 10 2005 036 763 A1. In this connection, a drawer that carries the sample container serves for loading and unloading the sample chamber, and a corresponding drawer mechanism is provided, with which the sample container can be moved into the sample chamber through an access opening of the incubator, which opening can be closed off with a cover, and, after the incubation procedure has been carried out, can be moved out of the sample chamber once again. In this connection, the drawer mechanism that bears the drawer and the cover is disposed and mounted, at least in part, within the sample chamber.

Because of the placement and installation of the drawer mechanism within the sample chamber, which exists at least in part, the drawer mechanism of such an incubator is frequently exposed to the possibly harmful atmosphere in the sample chamber, which is particularly contaminated by chemical or biological samples possibly partially evaporating within the incubator or by gases introduced into the sample chamber externally, and this makes regular cleaning of the drawer mechanism necessary, for one thing, and, for another thing—for example due to the corrosion processes that are promoted by this—is disadvantageous for the useful lifetime of a corresponding drawer mechanism. Furthermore, as a result, the sample chamber as such is also difficult and complicated to clean, because of the drawer mechanism that is disposed or installed in it, at least in part, and this also proves to be a disadvantage.

Furthermore, (external) robot systems are also known from the state of the art, with which a sample container (for example a microtiter plate for holding multiple samples at the same time) can be moved into the sample chamber of an incubator, set down there, and, after completion of the incubation process, moved out of the chamber again. In this connection, it is always provided that the robot system that serves as the insertion and removal mechanism reaches into the sample chamber when the access opening is open and must be moved out of the sample chamber again before the access opening is closed, which is a disadvantage, also in terms of time. Furthermore, commercially available robot systems are generally not suitable for setting down or picking up sample containers in a spatially restricted sample chamber, and therefore must be adapted to this or designed accordingly, with significant effort. Moreover, external robot systems frequently prove to be complicated to adjust and/or do not meet the demand that exists for an incubator that is as compact as possible, with an integrated insertion and removal mechanism.

Against this background, it is the task of the present invention to make available an incubator of the type stated initially, which is as compact as possible, easy to handle, and improved as compared with the state of the art, having an insertion and removal mechanism for loading and unloading the sample chamber, with which the disadvantages mentioned above are eliminated.

SUMMARY

This task is accomplished with an incubator according to the claims.

In this connection, it is provided, in addition to the characteristics that have already been mentioned in the introduction and are in accordance with the species, that the at least one insertion and removal mechanism is installed completely outside of the sample chamber and bears the sample container carrier inserted into the sample chamber even while the access opening is closed.

In other words, within the scope of the present invention, an incubator is therefore made available, having an insertion and removal mechanism for loading and unloading the sample chamber with the samples to be temperature-regulated, in suitable sample containers, in which incubator the insertion and removal mechanism installed outside of the sample chamber, in other words mounted or supported outside of the sample chamber, bears the sample container carrier situated within the sample chamber even while the access opening is closed. Therefore the entire holder (in other words the suspension or mounting) of the insertion and removal mechanism of the incubator is disposed outside of the sample chamber, in other words is isolated from the interior of the sample chamber by at least one sample chamber wall that delimits the sample chamber, which wall is advantageously installed within the incubator, in fixed manner.

In this way, it is guaranteed, on the one hand, that at least the holder of the insertion and removal mechanism, which is required for installation purposes, is not exposed, at any point in time, to the atmosphere that exists within the sample chamber. Furthermore, the insertion and removal mechanism is not installed within the sample chamber, for example on a sample chamber wall that delimits the sample chamber, and this also clearly simplifies cleaning of the sample chamber, because of better accessibility in this regard, and thereby also makes it possible to achieve more reliable sterility of the incubator. And finally, within the scope of the present invention, an insertion and removal mechanism that is easy to handle and can be implemented with a compact construction is made available, which mechanism permanently bears the sample container carrier that is situated within the sample chamber during an incubation procedure, in other words even during the incubation procedure, thereby making it unnecessary to set down or pull out the sample container carrier before closing the access opening of the sample chamber.

It is understood that within the scope of the present invention, different sample containers and sample container carriers that are or can be correspondingly adapted to them can be used; in particular—in the sense of the particularly preferred use of standardized sample containers—what are called microtiter plates (also called "microwell plates" or "microplates" in English) and sample container carriers adapted to them are used. Microtiter plates are essentially rectangular sample containers, generally produced from plastic, having a plurality of separate cavities (in English: "wells") arranged in rows and columns, to accommodate samples, which containers are either borne by the sample container carrier adapted to them, over their full area, or are held at least at an edge region.

In this connection, typical microtiter plates, which can advantageously be used within the scope of the present invention, possess 6, 12, 24, 48, 96, 384 or 1536 individual cavities, for example, for accommodating—biological and/or chemical—samples, which are introduced into the cavities in question by means of suitable pipettes (for example using a pipetting robot with multi-channel pipettes). In this connection, an incubator according to the invention can also be adapted to the use of what are called "deep-well microplates," in other words microtiter plates having comparatively deep cavities, by means of suitable dimensioning of the sample chamber and of the access opening.

The sample chamber of an incubator according to the invention can be temperature-regulated in suitable manner, for example by means of heating and/or cooling elements in the form of heating foils, Peltier and/or PTC elements, which heat the sample chamber walls and, as known from the state of the art, must be disposed at a suitable location within the incubator in order to achieve the most homogeneous temperature possible within the sample chamber, for example on the rear side of at least one sample chamber wall that delimits the sample chamber and does not face the interior of the sample chamber. Corresponding heating/cooling elements do not, however, have to lie directly against a sample chamber wall, but rather can also advantageously be brought into heat-conductive contact with the wall, for example by means of suitable heat pipes (for example having a flat structure) (what is called a "vapor chamber"), in order to achieve the most uniform temperature-regulation possible of the at least one sample chamber wall; it is evident that a person skilled in the art will also configure or select the geometry and the material of the sample chamber in the manner usual in the art.

For the remainder, an incubator according to the invention can also have, aside from suitable means for temperature regulation of the sample chamber, further means for targeted adjustment of further ambient conditions within the sample chamber, for example means for setting the humidity, means for supplying one or more different gases, means for exposing the samples to electromagnetic radiation (for example infrared or ultraviolet light, microwaves, etc.), to mention only a few examples.

A first preferred further development of an incubator according to the invention provides that the insertion and removal mechanism is not only installed completely outside of the sample chamber, but also—even when the sample chamber is closed, with the sample container carrier situated within the sample chamber—disposed completely outside of the sample chamber. Of course, in the sense of the invention, it must also be ensured that the sample container carrier disposed within the sample chamber while the access opening is closed is borne by the insertion and removal mechanism disposed outside of the sample chamber in suitable manner—for example by means of a suitable holder that penetrates the cover that closes off the access opening to the sample chamber, in part, if necessary—while at the same time, the required (thermal) closure of the sample chamber must be guaranteed.

In particularly preferred manner, it can be provided, within the scope of the present invention, that the at least one access opening is closed off by means of a cover, wherein the cover can advantageously be heated and/or cooled.

By means of a cover that can be heated and/or cooled, a particularly homogeneous temperature distribution can be made available within the sample chamber, which in turn can be temperature-regulated, wherein the heatability of the cover, in particular, can also effectively prevent the formation of condensate on the inside of the cover that closes off the access opening, facing toward the interior of the sample chamber, which formation would otherwise be possible.

In another further development of the present concept of the invention, it can be provided that the at least one cover for closing off an access opening is disposed on the at least one insertion and removal mechanism in such a manner that the cover closes off the access opening when the sample container carrier has been completely moved into the sample chamber. In other words, the insertion and removal mechanism of an incubator according to the invention, which is mounted or disposed outside of the sample chamber, advantageously bears not only the sample container carrier that can be moved into and out of the sample chamber through the access opening, but rather, at the same time, also the cover, with which the said access opening is closed off, advantageously in air-tight and gas-tight manner. In this way, it becomes evident that within the scope of the present invention, it can simultaneously be implemented that the insertion and removal mechanism can simultaneously be disposed outside of the sample chamber and can bear the sample container carrier disposed within the sample chamber, closed off by means of the cover.

Furthermore, it can advantageously be provided, within the scope of the invention, that the at least one insertion and removal mechanism is configured in the manner of a drawer, with two guides, wherein the two guides are disposed on the left and right side, each outside of a wall that delimits the sample chamber laterally, at approximately the same height, and wherein the sample container carrier is attached to a crossbeam that connects two rails of the insertion and removal mechanism guided in the two guides with one another. This allows a particularly compact construction of an incubator according to the invention, having an insertion and removal mechanism disposed outside of the sample chamber, wherein in this connection, it can preferably be provided that the cover is also attached to the crossbeam of the insertion and removal mechanism or mounted on it so as to pivot.

In this connection, the crossbeam is advantageously attached in an end region of the two rails that are guided laterally next to the sample chamber and can be moved out of and into the incubator housing accordingly, and advantageously always oriented horizontally and parallel to a housing front of the incubator. It—including the cover attached to it and the sample container carrier held on it—can thereby be moved, in advantageous manner, between a first position that leaves the access opening clear, and a second position that closes off the access opening by means of the cover. In the first position, the sample container carrier should, as is evident, be moved out of the sample chamber of the incubator to such an extent that a sample container can be placed on it or a sample container can be removed from it—either manually or by means of an external robot system. In the second position, the sample container carrier has been moved completely into the sample chamber, while the cover, which is also installed on the crossbeam, closes off the access opening. In this connection, a holder that connects the sample container carrier with the crossbeam can project, at least in part or in its entirety, through the cover that closes off the access opening, or can, in turn, be attached to the side of the cover that faces the sample chamber (and thereby indirectly on the crossbeam of the insertion and removal mechanism).

In this connection, it should be clarified that in the embodiment of an incubator according to the invention as explained above, the entire insertion and removal mechanism should be viewed as being disposed completely outside of the sample chamber, because the sample container carrier, the holder that attaches the sample container carrier to the crossbeam, and the cover should not be viewed as being part of the actual insertion and removal mechanism, in the sense of the invention, even if the said components might be structured to be integral with the other components of the insertion and removal mechanism. In this exemplary embodiment of the invention, the insertion and removal mechanism is instead formed by the guides, which are advantageously disposed in the incubator housing, by the rails guided in them, and by the crossbeam that connects the rails.

The crossbeam of the drawer-like insertion and removal mechanism of an incubator according to the invention, of the type as explained above, is advantageously formed from a material having the lowest possible heat conductivity, particularly preferably mantled with a (thermal) insulation, at least in certain regions.

It is evident that it is advantageous, in order to implement automated or automatable loading and unloading of an incubator according to the invention, if the (at least one) insertion and removal mechanism has (at least) one drive unit, for example one that can be controlled electronically or is driven by this unit, wherein the drive unit can advantageously be formed by an electric motor. Such a drive unit can then, in a preferred further development of the present invention, (also) be disposed completely outside of the sample chamber, thereby not being exposed to the possibly harmful atmosphere in the sample chamber, on the one hand, and, on the other hand, also not exposed directly to the possibly high temperature in the sample chamber.

A particularly practical embodiment of the present invention provides that the sample chamber is delimited or encapsulated, toward five sides, by means of at least one sample chamber wall disposed in fixed manner within a housing of the incubator, and toward the sixth side by means of an end cover having the at least one closable access opening. In this connection, the sample chamber is therefore delimited, for example at the bottom, at the top, at the rear, on the left and right side, by means of sample chamber walls installed in fixed manner within the incubator, wherein part or all of the sample chamber walls that border on one another can be configured integrally from a suitably shaped or suitably formed component. Sample chamber walls that are not configured in one piece with adjacent sample chamber walls are advantageously welded onto, formed onto, or at least suitably sealed relative to adjacent (side) walls. The sixth side of the sample chamber, which advantageously represents the front side of the incubator and in which the at least one access opening to the sample chamber is formed, is advantageously formed by an end cover—for example installed on the outer housing of the incubator—that is sealed relative to the sample chamber walls adjacent to it, in suitable manner. The at least one access opening configured in the end cover is suitably dimensioned for loading and unloading purposes of the sample chamber and can be closed off by means of a separate cover, which can be installed in the insertion and removal mechanism, for example.

In this embodiment of an incubator according to the invention, it can then be provided, in yet another preferred manner, that the at least one sample chamber wall—delimiting the sample chamber toward five sides—with the exception of perforations that might be provided in it to pass gases into the sample chamber and/or to pass sensors through into the sample chamber, does not have any further perforations and/or any add-on elements installed on the sample chamber wall or through the sample chamber wall. It is evident that in this manner, an incubator having a sample chamber that can be cleaned in particularly simple manner is made available.

In yet another preferred further development of this concept, it can then be provided that the at least one sample chamber wall has a smooth progression on its inner side that delimits the sample chamber, with rounded regions between the different sides of the sample chamber, thereby allowing even simpler and more reliable cleaning of the sample chamber.

It is particularly advantageous, within the scope of the present invention, if the at least one insertion and removal mechanism, the sample container carrier borne by the at least one insertion and removal mechanism, and the sample container do not stand in direct contact with the at least one sample chamber wall in any position of the insertion and removal mechanism. In this connection, the sample container carrier is therefore always borne by the insertion and removal mechanism in suspended manner, i.e. without any contact with the walls in the sample chamber firmly installed in the incubator, thereby particularly making it possible, in particular, to temperature-regulate a plurality of sample containers at the same time (and, if necessary, stacked one on top of the other) in one and the same sample chamber, without special installations in the sample chamber being required.

Furthermore, it can be provided, within the scope of the invention, that the sample chamber of the incubator has a plurality of access openings and a plurality of insertion and removal mechanisms each assigned to an access opening, so that one and the same sample chamber of the incubator can serve for simultaneous temperature regulation of the samples in different sample containers, wherein each insertion and removal mechanism advantageously bears precisely one sample container carrier for this purpose, and—together with the sample container borne on or with it, each in each instance—can move this carrier into the sample chamber and out of the sample chamber, through the respective access opening, in the sense according to the invention.

In this connection, it can be provided, for example, that the different access openings, the insertion and removal mechanisms assigned to them and/or the sample container carriers borne by the respective insertion and removal mechanisms differ and are adapted to different types of sample containers, but this is not compulsory.

And finally, in yet another preferred further development of such an incubator having a plurality of access openings and insertion and removal mechanisms assigned to these (for loading and unloading samples through the respective access opening), it is provided that the access openings of the sample chamber are configured in an end cover that delimits the sample chamber toward one side, wherein at least two interchangeable end covers having a different number of access openings and/or a different size of the access openings are assigned to the incubator.

In this way, an incubator can be adapted to different purposes of use by means of replacement of the end cover, for example if different types of sample containers are supposed to be temperature-regulated with it. Thus, for example, a first of two interchangeable end covers can have a first plurality (for example two, four, six, etc.) of access openings for simultaneously loading the sample chamber of the incubator with the said plurality of usual "microplates," while a second (replacement) end cover has a lower number (for example one, two, three, etc.) of access openings, which are larger as compared with the access openings in the first end cover, for loading the incubator with "deep-well microplates" that are clearly higher as compared with conventional "microplates."

Because now only a smaller number of insertion and removal mechanisms are required for operation of the incubator after replacement of the first end cover with the second (having a smaller number of access openings), it is particularly advantageous, within the scope of this concept, if, in this connection, at least a part of the insertion and removal mechanisms—preferably without the tool insert—can be removed in such a manner that after the reduction in the number of access openings has taken place, now only those insertion and removal mechanisms remain functional or installed, with which the (reduced number of) remaining access openings can be charged.

In the case of access openings of different sizes in the different (replacement) cover plates, it is evident that the cover(s) closing off the respective access openings must then also be adaptable to the access openings of different sizes, if applicable, or replaceable with suitably dimensioned (replacement) covers.

Within the scope of this concept according to the invention, a set composed of an incubator according to the invention with two different (replacement) end covers and, if applicable, different (replacement) covers for closing off the access openings of different sizes in the different end covers, if applicable, may then be made available, thereby making it possible to adapt the incubator according to the invention to different requirement profiles in a simple manner.

BRIEF DESCRIPTION OF THE DRAWINGS

In the following, an exemplary embodiment of the invention will be explained in greater detail using the drawings.

FIG. 2 shows a perspective view of the incubator from FIG. 1 with the insertion and removal mechanisms completely moved in, FIG. 5 shows a further exemplary embodiment of an incubator according to the invention, having only two installed insertion and removal mechanisms and an end cover modified as compared with the incubator from FIG. 1.

DETAILED DESCRIPTION OF THE PREFERRED EMBODIMENTS

Figure 1:
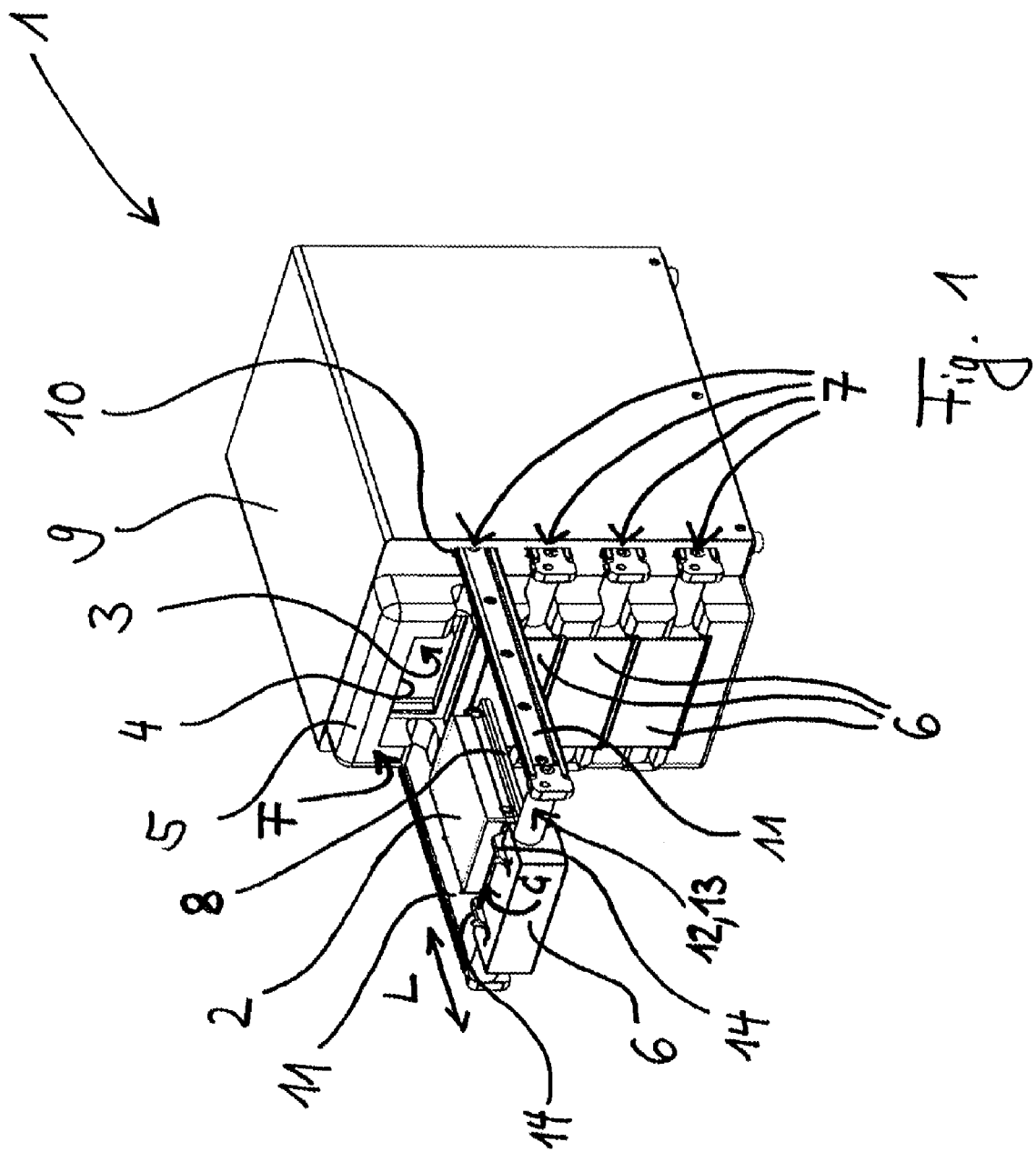
FIG. 1 shows a perspective view of an exemplary embodiment of an incubator according to the invention, having a total of four insertion and removal mechanisms, of which, in the present case, the uppermost mechanism is situated in a completely moved-out position.

The exemplary embodiment of an incubator 1 according to the invention, shown in different views in FIG. 1-4, as explained above, serves for simultaneously exposing samples, accommodated in a total of four sample containers 2, to a specific specifiable temperature. For this purpose, the incubator 1 has a temperature-regulatable sample chamber 3, which is accessible from a front side F of the incubator 1 by means of a total of four closable access openings 4.

In this connection, the access openings 4 are configured in an end plate 5 that delimits the sample chamber 3 toward the front side F, and are each tightly sealed by means of covers 6 suitably adapted for this purpose.

The incubator 1 furthermore has a total of four insertion and removal mechanisms 7—configured in drawer-like manner in the present case—which each bear a sample container carrier 8 and with which the sample container carrier 8 can be moved into the sample chamber 3 through the access opening 4 assigned to the respective insertion and removal mechanism 7 and moved out of the chamber. Each sample container carrier 8 in turn is set up for accommodating or bearing one sample container 2 each. Each of the total of four insertion and removal mechanisms 7, in the present case, is installed completely outside of the sample chamber 3 and disposed outside of the sample chamber 3 and, in this connection, comprises two guides 10—each disposed at the same height of the incubator 1—which are disposed on the left and right side outside of a wall 21, 22 (see FIG. 4) that delimits the sample chamber 3 laterally. A rail 11 is guided in these guides 10, in each instance, so as to be linearly movable according to the double arrow L, wherein the two rails 11 of the respective insertion and removal mechanism 7 are connected with one another in stable manner by means of a crossbeam 12, in an end region of the respective rail 11 that projects out of the outer housing 9 of the incubator 1.

Both the cover 6 that closes off the respective access opening 4 in the end cover 5 and the sample container carrier 8 that extends from the crossbeam 12 in the direction toward the sample chamber 3 are mounted on the crossbeam 12 of the respective insertion and removal mechanism 7, which is mantled with an insulation 13 in certain sections, wherein the sample container carrier 8 is firmly attached to the crossbeam 12 by means of two holding clamps 14, in each instance.

Figure 3:
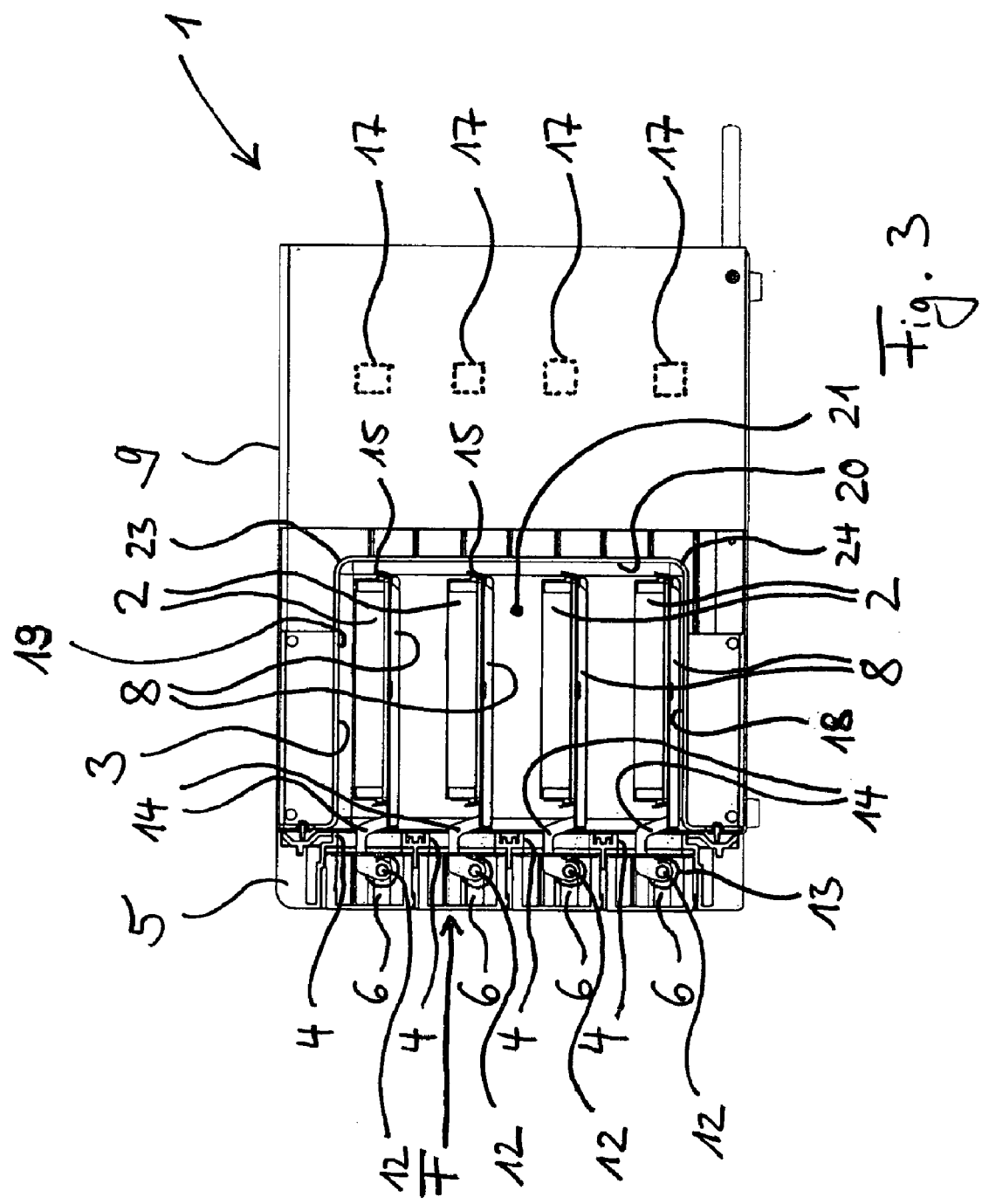
FIG. 3 shows a partial section through the incubator from FIG. 2, along the section line III-III there.

The sample container carriers 8, as is particularly well evident in FIG. 3, are held on the crossbeam 12 of the insertion and removal mechanism 7 that is always situated outside of the sample chamber 3, even when the sample container carrier 8 has been moved completely into the sample chamber 3 and the respective access opening 4 has been closed off by means of the cover 6 in question.

In order to guarantee a stable hold of the sample containers 2, which are configured as microtiter plates or "microplates" in the present case, on top of or on the side of the sample container carrier 8, holding elements 15 that are or can be adapted, in terms of their position, to the geometry of the sample container 2 to be used and are suitably biased there, under spring force, are provided.

The total of four covers 6 are mounted in the crossbeam 12 of the respective insertion and removal mechanism 7 so as to pivot about the longitudinal axis of the mechanism, according to arrow C. Suitable stops and guide elements on the incubator 1 or on the insertion and removal mechanism 7 of the incubator 1 ensure that the cover 6 completely closes off the access opening 4 assigned to it, when the sample container carrier 8 has been completely moved in by means of the insertion and removal mechanism 7, in an upright position, and that the cover 6 tilts about a pivot axis predetermined by the crossbeam 12—advantageously by about 90° into a horizontal position—directly at the beginning of moving out the sample container carrier 8 from the sample chamber 3, as is shown in the representation of the incubator 1 from FIG. 1, in the uppermost insertion and removal mechanism 7 there, which has been moved out completely.

Opening of the respective access opening 4 of the sample chamber 3 is facilitated by means of the pivoting of the cover 6 that initially takes place when the insertion and removal mechanism 7 is moved out, because as a result, the cover 6 is successively raised up and tilted away from the access opening 4, so that sudden opening of the access opening 4 can be reliably prevented.

Figure 2:
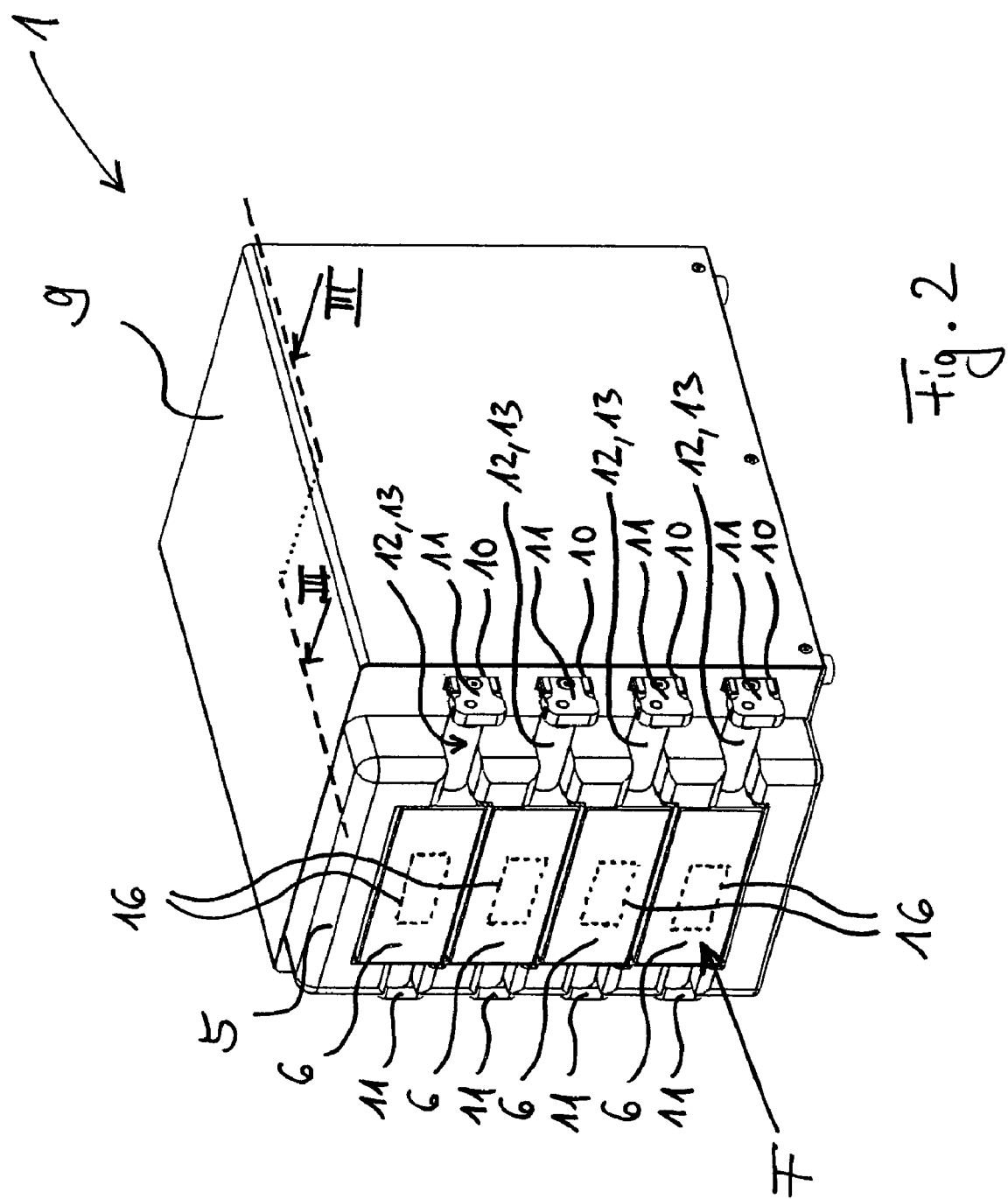

In FIG. 2, it is schematically indicated that a heating and/or cooling element 16, for example in the manner of a PTC element, can be installed in the respective covers 6, thereby making it possible to prevent the formation of condensate on the inside of the cover, particularly by means of heating of the inside of the respective cover 6 that faces toward the sample chamber 3.

The rear part of the incubator 1, not shown in cross-section in FIG. 3 (according to the section line III-III from FIG. 2 that runs at an angle), serves to accommodate its electronics, not shown, as well as to accommodate—drive units 17 shown with a broken line (e.g. electric motors)—for automated drive of the rails 11 guided in the guides 10 of the respective insertion and removal mechanism 7, which are not shown in FIG. 3 because of how the section line runs.

The sample chamber 3 of the incubator 1 is delimited toward five sides, namely at the bottom, at the top, at the rear, on the left and right side, by means of sample chamber walls 18, 19, 20, 21, 22 installed in the incubator 1 in fixed manner (see FIGS. 3 and 4), which walls, in the present example, are all configured to be smooth, without perforations and with rounded regions 23, 24 between the different sides. It is evident that the different sample chamber walls 18, 19, 20, 21, 22 can be produced, at least in part, from one and the same component.

Figure 4:
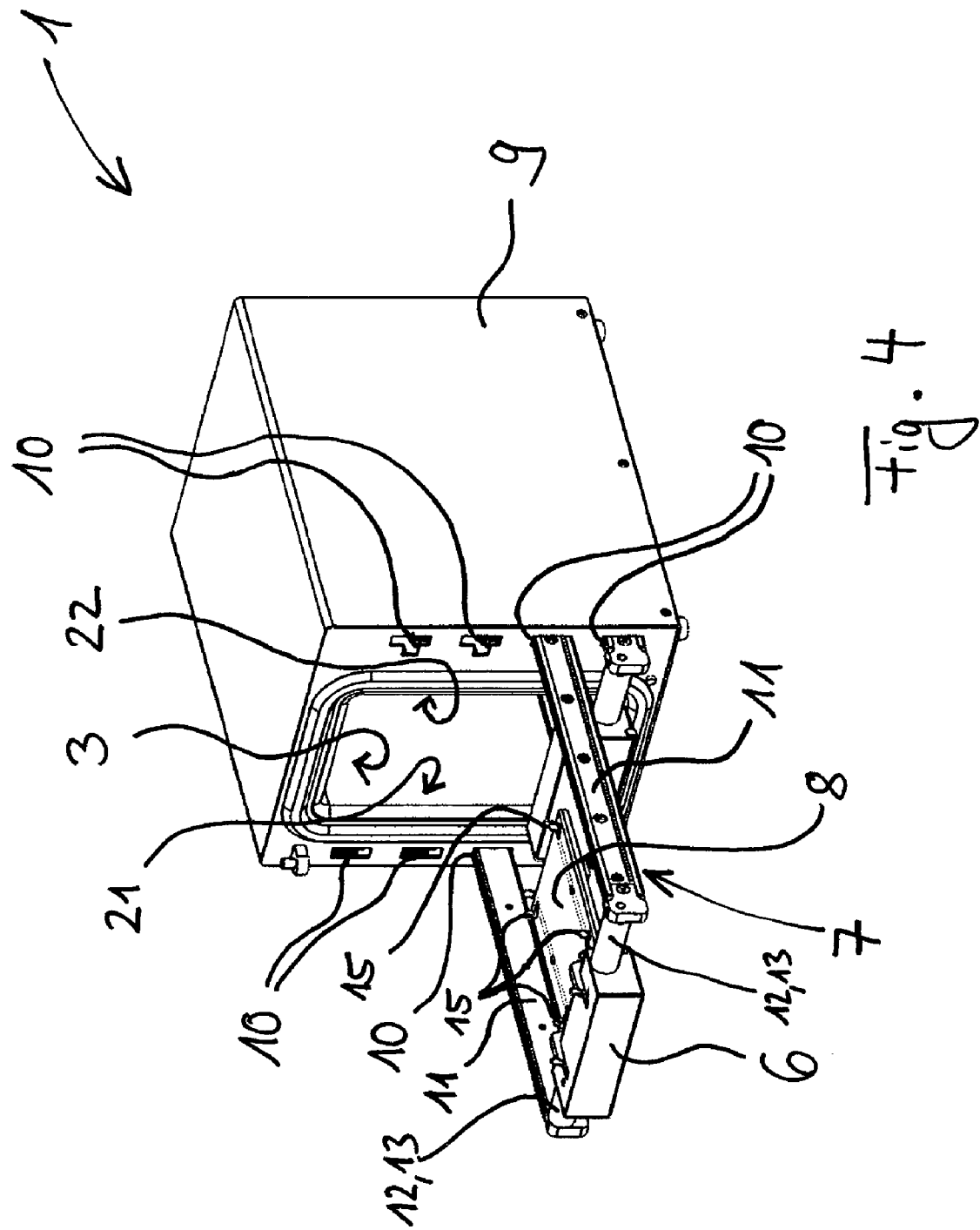
FIG. 4 shows a further representation of the incubator from FIG. 1, with the end cover left out and two insertion and removal mechanisms left out, for the sake of clarity.

In the representation of the incubator according to FIG. 4 (with the end cover 5 not shown, and two insertion and removal mechanisms also not shown or partially disassembled), it can be seen well that within the scope of the present invention, an incubator 1 having at least one integrated insertion and removal mechanism 7 can be implemented, the sample chamber 3 of which is particularly easy to clean, because of the installation and placement of the (at least one) insertion and removal mechanism 7 outside of the sample chamber 3, as described above.

If the rails 11 of the respective extraction mechanism 7, guided in the guides 10, and the end plate 5 that delimits the sample chamber 3 toward the front side can be disassembled in particularly simple manner, particularly without the use of tools, the sample chamber 3—which has a completely smooth progression and advantageously no perforations—is accessible for cleaning purposes, in particularly simple manner.

It is understood as a matter of course that an incubator 1 according to the invention does not necessarily need to have precisely four, but rather also a greater or smaller number, particularly also only one access opening 4 to the sample chamber 3, which can be charged with samples by means of a corresponding insertion and removal mechanism 7.

In this connection, FIG. 5 shows an incubator 1', which is essentially identical in construction to the incubator 1 from FIG. 1-4. It differs from the latter only in that it has a differently structured (replacement) end plate 5 for front-side delimitation of the sample chamber 3, having a lesser number of access openings, which are, however, larger, and correspondingly adapted (replacement) covers 6', which are suitable for moving in and moving out a total of two "deep-well microplates." Furthermore, in the case of the incubator 1' from FIG. 5, only two of the actually four insertion and removal mechanisms 7 are needed, so that the unneeded two insertion and removal mechanisms 7 were partially disassembled by means of removing the respective rails 11 from the corresponding guides 10. The openings of the non-needed guides 10 that remain in the outer housing 9 of the incubator 1 when this is done are covered by corresponding covers 25, in order to prevent penetration of dirt into the guide 10—which are located outside of the sample chamber 3.

What is claimed is:

1. An incubator (1) for exposing samples accommodated in sample containers (2) to a specifically specifiable temperature, comprising
   a temperature-regulatable sample chamber (3), which has at least one closable access opening (4), and
   at least one insertion and removal mechanism (7), which bears a sample container carrier (8) and by means of which the sample container carrier (8), which in turn bears a sample container (2), can be moved into the sample chamber (3) and out of the latter through an access opening (4) of the incubator (1),
   wherein the at least one insertion and removal mechanism (7) is completely outside of the sample chamber (3) and bears the sample container carrier (8) inserted into the sample chamber (3) even while the access opening (4) is closed.

2. The incubator of claim 1, wherein the at least one insertion and removal mechanism (7) is disposed completely outside of the sample chamber (3).

3. The incubator of claim 1, wherein the at least one access opening (4) is closed off by means of a cover (6), wherein the cover (6) can advantageously be heated or cooled.

4. The incubator of claim 3, wherein the at least one cover (6) for closing off an access opening (4) is disposed on the at least one insertion and removal mechanism (7) in such a manner that the cover (6) closes off the access opening (4) when the sample container carrier (8) has been completely moved into the sample chamber (3).

5. The incubator of claim 1, wherein the at least one insertion and removal mechanism (7) is configured in the manner of a drawer, with two guides (10), wherein the two guides (10) are disposed on the left and right side, each outside of a wall (21, 22) that delimits the sample chamber (3) laterally, at approximately the same height, and wherein the sample container carrier (8) is attached to a crossbeam (12) that connects two rails (11) of the insertion and removal mechanism (7) guided in the two guides (10) with one another.

6. The incubator of claim 5, wherein the cover (6) is attached to the crossbeam (12) of the insertion and removal mechanism (7) or mounted on it so as to pivot.

7. The incubator of claim 6, wherein the crossbeam (12) is mantled with insulation (13), at least in certain regions.

8. The incubator of claim 1, wherein the at least one drive unit (17) that drives the at least one insertion and removal mechanism (7) is disposed completely outside of the sample chamber.

9. The incubator of claim 1, wherein the sample chamber (3) is delimited toward five sides by means of at least one sample chamber wall (18, 19, 20, 21, 22) disposed in fixed manner within a housing (9) of the incubator (1) and toward the sixth side by means of an end cover (5, 5') having the at least one closable access opening (4).

10. The incubator of claim 9, wherein the at least one sample chamber wall (18, 19, 20, 21, 22), with the exception of perforations that might be provided in it to pass gases into the sample chamber (3) or to pass sensors through into the sample chamber (3), does not have any further perforations or any add-on elements installed on the sample chamber wall (18, 19, 20, 21, 22) or through the sample chamber wall (18, 19, 20, 21, 22).

11. The incubator of claim 9, wherein the at least one sample chamber wall (18, 19, 20, 21, 22) has a smooth progression on its inner side that delimits the sample chamber (3), with rounded regions (23, 24) between the different sides of the sample chamber (3).

12. The incubator of claim 1, wherein the at least one insertion and removal mechanism (7), the sample container carrier (8) borne by the at least one insertion and removal mechanism (7), and the sample container (2) do not stand in direct contact with the at least one sample chamber wall (18, 19, 20, 21, 22) in any position of the insertion and removal mechanism (7).

13. The incubator of claim 1, wherein the sample chamber (3) of the incubator (1) has a plurality of access openings (4) and a plurality of insertion and removal mechanisms (7) each assigned to an access opening (4).

14. The incubator of claim 13, wherein the access openings (4) of the sample chamber (3) are configured in an end cover (5) that delimits the sample chamber (3) toward one side, wherein at least two interchangeable end covers (5, 5') having a different number of access openings (4) or a different size of the access openings (4) are assigned to an incubator (1).

* * * * *